United States Patent [19]

Jequier et al.

[11] Patent Number: 5,489,684
[45] Date of Patent: Feb. 6, 1996

[54] PROCESS FOR THE PREPARATION OF (6S)-5,6,7,8-TETRAHYDROFOLIC ACID

[75] Inventors: Pascal Jequier, Melide; Fabrizio Marazza, Novaggio, both of Switzerland

[73] Assignee: Sapec S.A. Fine Chemicals, Lugano, Switzerland

[21] Appl. No.: 159,542

[22] Filed: Dec. 1, 1993

[30] Foreign Application Priority Data

Dec. 1, 1992 [CH] Switzerland .................... 03674/92

[51] Int. Cl.$^6$ .................................... C07D 425/04
[52] U.S. Cl. .................................... 544/258
[58] Field of Search .................................... 544/258

[56] References Cited

U.S. PATENT DOCUMENTS

| | | | |
|---|---|---|---|
| 4,929,551 | 5/1990 | Eguchi | 435/106 |
| 5,006,655 | 4/1991 | Mueller | 544/258 |
| 5,010,194 | 4/1991 | Mueller | 544/258 |
| 5,194,611 | 3/1993 | Marazza et al. | 544/258 |
| 5,239,074 | 8/1993 | Marazza et al. | 544/247 |
| 5,324,836 | 6/1994 | Mueller et al. | 544/258 |
| 5,382,581 | 1/1995 | Marazza et al. | 544/258 |
| 5,391,738 | 2/1995 | Vecchi | 544/258 |

FOREIGN PATENT DOCUMENTS

| | | |
|---|---|---|
| 0495204A1 | 12/1991 | European Pat. Off. . |
| 0539987A2 | 10/1992 | European Pat. Off. . |
| 0038285 | 3/1983 | Japan ............. 544/258 |
| 9315076 | 8/1993 | WIPO ............. 544/258 |

OTHER PUBLICATIONS

A. Hilio et al. Chem Abstr vol. 120 entry 288693 Abstracting EP 539987 (1993).

Kenneth O. Donaldson, et al., "Naturally Occurring Forms of Folic Acid," *The Journal of Biological Chemistry*, vol. 237, No. 12, Dec. 1962.

Esam Khalifa, et al., "Eine einfache Synthese von Leucovorin," *Helvetica Chimica Acta*, vol. 63, Fasc. 8 (1980)–Nr. 272 pp. 2554–2558.

V. S. Gupta, et al., "Preparation and Properties of Crystalline 5-Methyl Tetrahydrofolate and Related Compounds," *Archives of Biochemistry and Biophysics* 120, 712–718 (1967).

*Primary Examiner*—Donald G. Daus
*Attorney, Agent, or Firm*—Burns, Doane, Swecker & Mathis

[57] ABSTRACT

(6S)-THF is obtained by adding, in portions, an acid to an aqueous solution of a (6RS)-diastereoisomeric mixture of an alkali metal salt of 5,6,7,8-tetrahydrofolic acid. The addition is made at a temperature from 5° C. to 80° C. for the purpose of the selective crystallization for a period sufficient to stabilize the pH to a value of from 4.8 to 5.3. Then, the formed solid, i.e., (6S)-5,6,7,8-tetrahydrofolic acid, is separated.

10 Claims, No Drawings

PROCESS FOR THE PREPARATION OF (6S)-5,6,7,8-TETRAHYDROFOLIC ACID

The present invention is directed to a process for the preparation of (6S)-5,6,7,8-tetrahydrofolic acid. In this regard, 5,6,7,8-Tetrahydrofolic acid is frequently referred to herein as "THF".

(6S)-THF may be used as a starting material for the preparation of (6S)-N(5)-formyl-THF, (6S)-N(5)-methyl-THF and (6R) -N (5) ,N (10) -methylene-THF.

BACKGROUND OF THE INVENTION

A synthesis of diastereoisomeric pure reduced folates, as well as their importance in the pharmaceutical field, are described in European Patent Application No. 91 905 831.32101, publication No. 0 471 820.

In European Patent Application No. 91 121 326.2, publication No. 0 495 204 A1, there is described, among other things, a process for the preparation of (6S)- and (6R)-tetrahydrofolic acids using fractional crystallization of their corresponding acid addition salts with a sulfonic acid or with sulfuric acid. There is no disclosure of a direct, selective crystallization of (6S)-THF in the form of the free acid.

It is believed that the process described in EP 0 495 204 A1 contains certain unnecessary steps, such as the preparation of the acid addition salts and their transformation into free acids. For example, according to the embodiments described in the examples of the document, fractional crystallization of acid addition salts must always be carried out in the presence of an antioxidant, such as mercaptoethanol.

The process is not economical, and is detrimental to the environment. For example, at least one equivalent of a sulfonic acid salt or of a sulfuric acid salt is formed as by-product during liberation of the acid from the acid addition salt, which must be disposed of.

A direct, selective crystallization of (6S)-THF in the form of the free acid has not yet been described.

SUMMARY OF THE INVENTION

Accordingly, it is an object of the present invention to provide an improved process for the preparation of (6S)-THF, using a direct, selective crystallization of (6S)-THF in the form of the free acid; e.g., a process which does not require the aforementioned unnecessary steps of, and avoids the problems associated with, the process described in EP 0 495 204 A1.

More particularly, the invention is directed to a process for the preparation of (6S)-5,6,7,8-tetrahydrofolic acid, i.e., (6S)-THF, of formula (I):

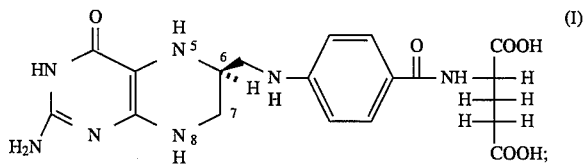

having a diastereoisomeric purity of at least 75%. The process comprises adding, in portions, an acid to an aqueous solution of a (6RS)-diastereoisomeric mixture of an alkali metal salt of 5,6,7,8-tetrahydrofolic acid at a temperature from 5° C. to 80° C., for a sufficient time to stabilize the pH to a value of from 4.8 to 5.3, preferably 4.9 to 5.2, and most preferably 5.0, while selectively crystallizing the desired product. Then, the resulting formed solid is separated; i.e., (6S)-5,6,7,8-tetrahydrofolic acid.

As will be evident from the discussion and examples provided below, it has been surprisingly found that the objects and advantages of the invention, particularly selective crystallization, can be obtained through the addition of the acid to the diastereoisomeric mixture at a temperature of from 5° C. to 80° C., and stabilizing the pH at a value of from 4.8 to 5.3.

DETAILED DESCRIPTION OF THE PREFERRED EMBODIMENTS

The acid to be added to the (6RS)-diastereoisomeric mixture of THF is preferably selected from the group consisting of hydrohalic acids, especially hydrochloric acid, sulfuric acid, phosphoric acid, acetic acid, trichloroacetic acid, trifluoroacetic acid, methanesulfonic acid, p-toluenesulfonic acid, especially aqueous solutions of these acids.

In a preferred embodiment, the addition of acid and the simultaneously occurring selective crystallization are realized at a temperature from 40° C. to 50° C. Also preferably, the whole reaction is carried out under inert gas atmosphere.

The aqueous solution of the (6RS)-diastereoisomeric mixture can additionally contain at least one complexing agent for heavy metals, preferably selected from the group consisting of ethylene diamine tetraacetic acid (EDTA), and its salts and hydrates, especially its di-sodium salt, nitrilotriacetic acid, and 1,2-diaminocyclohexane-N,N,N', N'-tetraacetic acid. EDTA and its di-sodium salt are preferred.

The starting material used in the inventive process, for example, a di-sodium salt of (6RS)-THF, may be prepared according to the teachings of E. Khalifa et. al., Helv. Chim. AcTA (1980), 63, 2554.

The starting material may also be obtained by suspending the (6RS)-diastereoisomeric mixture of THF, preferably in the presence of the di-sodium salt of ethylenediaminetetraacetic acid (EDTA), in water under an inert gas atmosphere at a temperature of about 35° C., and adding an aqueous sodium hydroxide solution, drop-by-drop, for a sufficient time to provide a homogenous solution. This solution will typically have a pH-value of about 6.5. To increase stability, it is advantageous to adjust the pH-value of the solution to a value from 5.5 to 5.0 by adding one of the preferred acids.

The solution should then be warmed, preferably to a temperature from 40° C. to 50° C. more preferably 45° C. Then acid is added drop-by-drop to selectively crystallize (6S)-THF, for a time sufficient to stabilize the pH to a value of from 4.8 to 5.3, preferably 4.9 to 5.2, most preferably 5.0.

There will be observed a formation of a crystalline solid during the addition of the acid. Selective crystallization will usually be complete after about one hour.

The crystalline solid can then be separated by, for example, filtration or centrifugation, and then washed and dried in a conventional manner.

At values below the lower end of the recited pH range of 4.8 to 5.3, e.g., at 4.5, there is observed a lower crystallization selectivity of (6S) versus (6R); although a relatively high yield is obtained. In contrast, at a pH of 5.0, crystallization selectivity is better (although yield is lower). Exemplary data showing the significance of the recited parameters is provided below.

TABLE 1

| PH-value | Temperature | Ratio (6S)/(6R)-THF | Yield % |
|---|---|---|---|
| 5.2 | 35° C. | 80:20 | 45 |
| 5.0 | 25° C. (14h) | 77:23 | 54 |
| 4.8 | 40° C. | 75:25 | 54 |
| 4.5 | 45° C. | 67:33 | 67 |
| 5.0 | 50° C. | 80:20 | 48 |
| 4.5 | 70° C. | 64:36 | 55 |
| 5.0 | 45° C. | 80.5:19.5 | 48 |

For obtaining diastereoisomeric pure (6S)-THF, the inventive process may be carried out several times.

The following table illustrates the crystallization of a diastereoisomeric mixture of 80% (6S)- and 20% (6R)-THF at different temperatures and pH-values.

TABLE 2

| pH-value | Temperature | Ratio (6S)/(6R)-THF | Yield % |
|---|---|---|---|
| 5.0 | 50° C. | 89:11 | 86 |
| 5.6 | 25° C. | 94:6 | 66 |
| 5.2 | 45° C. | 92:8 | 75 |

If desired, (6R)-THF may be obtained from the mother liquor. For this, one equivalent of a calcium salt, for example, a calcium halide such as calcium chloride or calcium bromide, or calcium acetate, referred to in terms of the present amount of THF, is added as a solid to the mother liquor. Thereafter a base is added, for example, an aqueous sodium hydroxide solution, until a pH-value of about 6.0 is obtained.

The solution is partially concentrated, for example, to a concentration of 10% of THF in the concentrated solution. From this concentrated solution crystallizes (6R)-THF in the form of a calcium salt in about two hours.

The following examples illustrate the present invention, but should not be interpreted as limiting the invention in any way.

Example 1

100 g of (6RS) -5,6,7,8-tetrahydrofolic acid, prepared according to E. Khalifa et al. Helv. Chim AcTa, (1980), 63, 2554, and 2.0 g of the di-sodium salt of ethylene diamine tetraacetic (EDTA) were suspended in 750 ml of water under a nitrogen atmosphere at a temperature of 35° C.

There was added, drop-by-drop, a 20% aqueous sodium hydroxide solution for a time until a homogenous solution was obtained. This solution had a pH-value of 6.5.

The mixture was then stirred vigorously. By the addition, drop-by-drop, of 18% aqueous hydrochloric acid, the pH was adjusted to a value of 4.8. Then the temperature was increased to 45° C. After a few minutes at that temperature there was observed the formation of a crystalline solid. At that time the pH-value of the suspension began to increase simultaneously.

By the addition of 18% aqueous hydrochloric acid the pH-value was maintained at 5.0 until the value had stabilized after about 45 minutes.

The white crystalline solid was isolated by means of filtration, washed once with water and once with acetone. Then the solid was dried under reduced pressure at a temperature of 50° C.

In this manner there was obtained 48 g of crystalline 5,6,7,8-tetrahydrofolic acid.

For determining the diastereoisomeric ratio, a sample of the obtained product was transformed into N(5)-$CH_3$-THF according to K.O. Donaldson and Keresztesy J.C., J. Biol. Chem., (1962), 237, 3815 or V.S. Gupta and F.M. Huennekens, Arch. Biochem. Biophys. (1967), 120, 712. The so obtained product was then analyzed on a chiral column (RESOLVOSIL).

A diastereoisomeric ratio of (6S)/(6R)=80.5/19.5 was determined.

HPLC-analysis (reverse phase-column): 99.3%

Water content according to Karl Fischer: 7.5%

Chloride content: 0%

Example 2

A 40 g sample of the product obtained according to example 1 was suspended in 500 ml of water and treated in a manner analogous to that of Example 1.

Selective crystallization of the free acid was realized at a pH-value of 5.2.

There was obtained 30.2 g of crystalline 5,6,7,8-tetrahydrofolic acid having a diastereoisomeric ratio of (6s) / (6R) = 93/7.

HPLC-analysis (reverse phase-column): 99.1%

Water content according to Karl Fischer: 5.7%

$[\alpha]_D = -32.5°$ (C=1, 0.04 N NaOH, pH=9.5)

chloride content: 0%

| Elemental analysis | Calculated (%) | Found (%) |
|---|---|---|
| $C_{19}H_{23}N_7O_6 \cdot 1.5\ H_2O$ | C 48.32 | 48.59 |
| | N 20.76 | 21.06 |
| | H 5.55 | 5.57 |

While there are shown and described present preferred embodiments of the invention, it is to be understood that the invention is not limited thereto, but may be otherwise variously embodied and practiced within the scope of the following claims.

We claim:

1. A process for the preparation of (6S)-5,6,7,8-tetrahydrofolic acid according to formula (I):

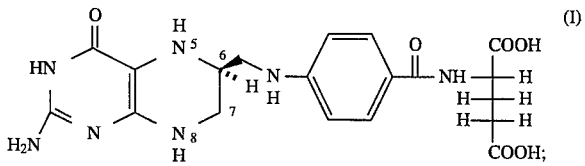

having a diastereoisomeric purity of at least 75%, said process conducted without fractional crystallization of acid addition salts, and comprising a direct crystallization from a (6RS)-diastereoisomeric mixture of an alkali metal salt of 5,6,7,8tetrahydrofolic acid wherein
(i) a strong non-oxidizing acid or acetic acid is added in portions over time to an aqueous solution of a (6RS)-diastereoisomeric mixture of an alkali metal salt of 5,6,7,8-tetrahydrofolic acid at a temperature from 5° C. to 80° C. and to an extent effective to adjust and stabilize the pH to a value of from 4.8 to 5.3 to directly and selectively crystallize (6S)-5,6,7,8-tetrahydrofolic acid, and (ii) the formed solid is separated, said solid being (6S)-5,6,7,8-tetrahydrofolic acid having a diastereoisomeric purity of at least 75%.

2. A process according to claim 1, wherein the aqueous solution of the (6RS)-diastereoisomeric mixture further comprises at least one chelating agent.

3. A process according to claim 2, wherein the aqueous solution of the (6RS)-diastereoisomeric mixture comprises ethylene diamine tetraacetic acid, a salt thereof or hydrate thereof, nitrilotriacetic acid, 1,2-diaminocyclohexane-N,N,N',N'-tetraacetic acid, or mixtures thereof.

4. A process according to claim 3, wherein the aqueous solution of the (6RS)-diastereoisomeric mixture comprises EDTA, its di-sodium salt, or mixtures thereof.

5. A process according to 1, wherein the addition of acid and the selective crystallization simultaneously occur and are realized at a temperature from 40° C. to 50° C.

6. A process according to claim 1, wherein the added acid is selected from hydrohalic acids, and mixtures thereof.

7. A process according to claim 1, wherein the added acid is selected from hydrochloric acid, sulfuric acid, phosphoric acid, acetic acid, trichloroacetic acid, trifluoroacetic acid, methanesulfonic acid, p-toluenesulfonic acid, aqueous solutions thereof, and mixtures thereof.

8. A process according to claim 1, wherein the pH value is stabilized to a value of from 4.9 to 5.2.

9. A process according to claim 8, wherein the pH value is stabilized to a value of about 5.0.

10. A process according to claim 1, wherein the whole reaction is carried out under inert gas atmosphere.

* * * * *